US00PP13607P29

(12) United States Plant Patent
Asadoorian

(10) Patent No.: US PP13,607 P2
(45) Date of Patent: Feb. 25, 2003

(54) GRAPEVINE DENOMINATED VARIETALLY F.P.C.D.O.V.#1

(75) Inventor: Alan J. Asadoorian, Fresno, CA (US)

(73) Assignee: Denken Farms, Fresno, CA (US)

( * ) Notice: Subject to any disclaimer, the term of this patent is extended or adjusted under 35 U.S.C. 154(b) by 134 days.

(21) Appl. No.: 09/814,249

(22) Filed: Mar. 21, 2001

(51) Int. Cl.[7] ..... A01H 5/00
(52) U.S. Cl. ..... Plt./205

(58) Field of Search ..... Plt./205

*Primary Examiner*—Bruce R. Campell
*Assistant Examiner*—W C Haas
(74) *Attorney, Agent, or Firm*—Wells St. John P.S.

(57) ABSTRACT

A new and distinct grapevine denominated varietally as F.P.C.D.O.V.#1 generally resembling in some regards the Thompson Seedless grapevine, but characterized as to novelty by producing grapes which are mature for harvesting or for cane cutting for DOV raisin production approximately 2 to 4 weeks ahead of the Thompson Seedless grapevine growing at Fresno, Calif.

1 Drawing Sheet

BACKGROUND OF THE NEW VARIETY

The present invention relates to a new and distinct variety of grapevine denominated varietally as F.P.C.D.O.V #1, and more particularly to a grapevine which is noted for its high fruitfulness, and the production of red colored seedless grapes having a berry size similar to that provided by the Thompson Seedless grapevine, but which ripens approximately 3 to 4 weeks earlier under the ecological conditions prevailing in the San Joaquin Valley of central California.

From a commercial standpoint, the relative times of ripening of various varieties of grapes is obviously extremely important. It has been recognized as desirable to provide grape vines that bear fruit earlier than varieties which it most nearly resembles whereby the fruit can be brought to market at a time when competition is at a minimum. In addition, if the ripening of various grape varieties can be spread over a longer period of time, savings, and increased efficiency can be obtained because the capital outlay which is generally required to harvest and then transport these grapes or resulting raisins which are harvested within a relatively short ripening period can be spread over longer periods of time resulting in lower costs of final production and further increasing the uniformity of production.

In a continuing effort to upgrade the quality of his grapevines which produce grapes for raisin production, the Applicant routinely crosses various grapevine varieties and thereafter evaluates the offspring to determine their suitability for various markets. In this regard, the applicant crossed two grapevine varieties in 1991 at a property which is located at 4415 E. American Avenue, Fresno, Calif. 93725.

ORIGIN AND ASEXUAL REPRODUCTION OF THE NEW VARIETY

The new variety of grapevine was produced through an intraspecific hybridization which took place on the inventor's property noted above, and which included a Ruby Seedless as the male parent (pollen), and an unnamed variety which was then growing in the inventor's vineyard as the female parent. This cross pollenation was done in 1991. The variety was subsequently evaluated and selected from among 500 resulting seedlings. These selected seedlings were then evaluated on the property which is located on the southwest corner of American and Minnewawa Avenues which is located southeast of Fresno, Calif. The inventor subsequently confirmed the characteristics of the new grapevine by asexually reproducing four new plants by dormant cuttings taken from the original seedling. These were propagated at the property of the inventor at 4415 E. American Avenue, Fresno, Calif. These subsequent asexually reproduced plants have been found to have the same distinctive features of the original plant, that is notably high fruitfulness and the production of red colored seedless grapes having a berry size similar to that produced by the Thompson Seedless grapevine but which ripens approximately 3 to 4 weeks earlier. This novel variety of grapvine is viewed as being a particular desirable variety for raisin production due in part to its early ripening characteristics relative to the Thompson Seedless. In this regard, the early ripening feature is favorable with respect to a drying-on-the-vine technique (DOV), a relatively new commercial method of drying grapes into raisins.

In addition to the foregoing, and based upon fruit maturation record collected during the 2000 growing season, the present grapevine variety is somewhat similar in its ripening characteristic to the Diamond Muscat grapevine (a USDA 1999 introduction which ripens approximately 3½ weeks ahead of the Thompson Seedless grapevine); at least one week earlier than the DOVine (a 1995 USDA introduction which ripens approximately 2½ weeks ahead of the Thompson Seedless); and 2 weeks earlier than the Fiesta grapevine (a 1973 USDA introduction which ripens approximately 1½ weeks ahead of the Thompson Seedless grapevine) under the growing conditions prevailing in the San Joaquin Valley of central California. The ripening data, noted above, was collected in research trials conducted at the University of California Kearney Agricultural Center which is located in Parlier, Calif. The soil and growing conditions at the Kearney Agricultural Center are quite similar to those where the new variety was first grown and evaluated. Still further, the new variety of grapevine is notably distinct from the fruit produced by the Ruby Seedless grapevine with respect to its berry shape and ripening date. Still further, the Ruby Seedless grapevine produces fruit which has a distinctly ovoid berry as compared to the described variety's round berry. Moreover, the Ruby Seedless grapevine is considered a late to mid-season variety, that is the ripening date of the Ruby Seedless is in late August, through mid September, under the ecological conditions prevailing in the vicinity of Fresno, Calif. This date of ripening of the Ruby Seedless grapevine is approximately 4 weeks later than the present variety.

BRIEF DESCRIPTION OF THE DRAWING

The accompanying drawing is a color photograph of two bunches of grapes of the subject variety both of which show the grapes sufficiently mature on the one hand for harvesting or shipment, or for further raisin production (DOV) as referenced above. Several leaves are further shown to illustrate their dorsal and ventral coloration; a typical section of vine is also provided; all of these are of the instant variety.

DETAILED DESCRIPTION

Referring more specifically to the pomological details of this new and distinct variety of grapevine, the following has been observed under the ecological conditions prevailing at a commercial vineyard which is located near 4415 E. American Avenue, Fresno, Calif. 93725.

All major color code designations are by reference to The Dictionary of Color by Maerz and Paul, Second Edition, published in 1950. Common color names are also used occasionally.

Vine:

*Size.*—Generally — large.

*Form.*—Upright dense and tender; the subject variety was head-trained and cane-pruned.

*Vigor.*—Very vigorous.

*Primary shoot.*—Length — considered medium long, and averaging about 66 inches (168 cm). The shoot length may range between about 48 inches (122 cm) and 80 inches (203 cm).

*Shoots.*—Growth Habit — trailing and having medium to slender diameter and medium to long internodes. Normally lateral shoots develop at most nodes but are most often considered weak averaging only approximately 2 inches (5 cm).

*Lateral shoots.*—Length — variable, from approximately 1 inch (2.5 cm) to about 12 inches (30 cm). Lateral shoots have their best development on strong shoots which have an average length of approximately 3.5 inches (9 cm), and show their least development on smaller shoots (those having an average length of approximately 1.4 inches (3.5 cm)).

*Shoot bifurcation.*—Common. When bifurcation occurs both branches normally produce clusters. In 2000, 12% of the shoots bifurcated.

*Shoot tips.*—Texture — glaborous.

*Shoot tips.*—Color — light green (plate 20-L-4) and occasionally appearing with a light bronze color.

*Tendrils.*—Location — intermittent.

*Tendrils.*—Color — light green and slender.

*Tendrils.*—Length — considered medium-long.

*Canes.*—Surface Texture — finely ribbed.

*Color.*—Generally a uniform light medium-brown (plate 13-9-C) at full maturity, and having a light yellowish-green color (plate 17-6-D) when immature.

*Nodes.*—Size — slightly enlarged and having a reddish-brown pigmentation (plate 56-2-H) which normally appears at the bud and petiole base.

*Internode length.*—Approximately 2.4 inches (6 cm). This size may range between approximately 2.8 inches (7 cm) on very strong shoots, and approximately 2 inches (5 cm) on weak shoots.

*Cane diameter.*—Variable between approximately 0.24 inches to about 0.36 inches for very weak to very strong shoots.

*Bud fruitfulness.*—Generally — Fruitfulness is generally viewed as potentially 100%, or greater, when compared to the Thompson Seedless variety of grapevine growing in the same geographical area.

*Average clusters per node.*—Generally — Approximately 1.83 on average, on fruiting canes in the 2000 growing year. These numbers are greater than the Thompson Seedless grapevines growing in the same geographical area and which usually average approximately 0.6 to 1.0 clusters per node.

*Basal node.*—Generally — The first node has a lower percentage bud break (24%) and fruitfulness (0.7 clusters per shoot) than other nodes.

*Node numbers.*—Approximately 2 to about 14. About 77% to about 100% bud break occurred at these nodes, and further 1.1 to about 1.8 clusters per shoot were produced during the 2000 growing year.

*Renewal spurs.*—Numbers — Approximately 0.7 clusters per shoot in the 2000 growing year were produced from these spurs.

*Inflorescences.*—Color — light yellowish in color. This color, however, is not particularly distinctive of the variety.

*Stamens.*—Length — medium and considered upright.

*Bloom time.*—Slightly ahead of the Thompson Seedless grapevine in the same geographical area; approximately 2 days in the 2000 growing year.

*Percentage bloom.*—65% (approximately 65% of the calyptras cracked or dehisced).

*Date of bloom.*—May 5, 2000 under the ecological conditions prevailing in Fresno, Calif. Thompson Seedless grapevines growing near the test plot were only at about 50% bloom on the same date.

*Leaves.*—Size — Generally medium to large.

*Width.*—Approximately 6 inches (15.2 cm). This size is variable and ranges from about 4.3 inches (11 cm) to about 7.5 inches (19 cm).

*Length.*—About 5.8 inches (14.7 cm). This average length may range from about 3.9 inches (9.9 cm) to about 7.4 inches (18.8 cm).

*Leave blade midrib length.*—Approximately 4.2 inches (10.7 cm).

*Petiole length.*—Approximately 4.1 inches (10.4 cm).

*Inferior sinuses.*—Depth — medium and having a mostly narrow, open and concave base with an average depth of about 1.3 inches (3.3 cm), and further having a range of depth of about 0.87 inches to about 2.2 inches (2.2 cm to about 5.6 cm).

*Superior sinuses.*—Shape — are considered deep, narrow and overlapping with the base and are pointed to a concave shape.

*Superior sinuses.*—Depth — approximately 1.9 inches (4.8 cm) this depth ranges from about 1.4 to about 2.8 inches (3.6 to about 7.2 cm).

*Petiolar sinuses.*—Shape — lyre like and being moderately deep, approximately 1.6 inches (4.1 cm).

*Dorsal sufrace.*—Surface Texture — glabrous.

*Ventral surface.*—Surface Texture — generally considered glabrous except for short hairs that may be occasionally found on the main veins and their secondary branches. These hairs are not dense and they are very sparse on the smaller veins.

*Ventral surface.*—Overall Appearance — generally flat however slight waviness may appear between the main veins.

*Dorsal surface.*—Color — dark green (plate 22-D-12).

*Ventral surface.*—Color — light green (plate 20-E-7).

*Marginal form.*—Teeth — straight and having slightly convex sides. The teeth are considered medium in depth and range from about 0.6 to about 0.8 inches (0.2 to about 1.5 cm). The average depth is about 0.28 inches (0.7 cm). The teeth are considered narrow with an average height to width ratio of about 0.8:1.

Fruit:

*Maturity when described.*—Ripening begins (veraison) about 8 to 12 days ahead of the Thompson Seedless grapevines growing in the geographical vicinity of Fresno County, Calif. When compared with the Thompson Seedless grapevines growing in close vicinity to the test plot, the berries of the subject variety were 85% soft on Jun. 16, 2000, whereas the adjoining Thompson Seedless grapevines began to experience berry softening (1% soft) on Jun. 19, 2000.

*Full maturity.*—Considered early. The subject variety is mature at about 3 to 4 weeks earlier than the Thompson Seedless grapevines growing in the same geographical area. For example, the fruit of the subject variety averaged a 23.2° Brix on Aug. 1, 2000 while adjoining Thompson Seedless grapevines in an adjacent area averaged only 17.5° Brix.

*Cluster.*—Generally — the clusters, as a general matter, are viewed as being loose to well filled, and further have a long conical sometimes shouldered shape. Small wings are common. On occasion, large well developed wings may be found.

*Size.*—Generally — medium to large.

*Average weight.*—0.9 lbs. (409 grams). This weight may range between 0.4 to about 1.5 lbs. (182 to about 681 grams). This cluster weight is similar to that produced by the Thompson Seedless grapevine.

*Average cluster length.*—Approximately 9.65 inches (24.5 cm).

*Peduncles.*—Length — On average, approximately 1.25 inches (3.2 cm). The peduncles are considered of medium thickness, averaging approximately 0.16 inches (0.4 cm). The peduncles are occasionally lignified at their base.

*Berry shape.*—Considered round to slightly obovoid in shape.

*Berry length.*—Approximately 1.70 cm.

*Berry width.*—Approximately 1.52 cm.

*Berry length to width ratio.*—Approximately 1.12:1.

*Average berry weight.*—Approximately 1.92 grams. This weight ranges between about 0.9 to about 4.0 grams. Berry weight can be quite variable due to fluctuating weather conditions during bloom time.

*Berry color.*—Variable, in this regard, more sunlight-exposed and mature berries achieve a greater reddish color on a light to yellowish-green background (plate 20-E-1). Red pigmentation in the individual berries ranges from a purplish-red (plate 47-J-7) to well-colored berries which have a light rose color (plate 53-K-10). This color may be found on the partially or lighter colored berries.

*Berry flesh.*—Generally — firm and not considered juicy.

*Berry juice.*—Generally — clear and having a sweet neutral flavor and aroma.

*Brush attachment.*—Considered strong. For example when the pedicel is removed an average of about 0.4 cm of the flesh is also removed with same.

*Flesh.*—Generally— Each berry contains approximately 2 to about 4 very small seed traces. On average approximately 2.6 seed traces are found. These seed traces have a size and consistency similar to the Thompson Seedless and that found in the Fiesta grapevines. Seed traces are usually pink in color. This color is not particularly distinctive.

*Seed traces.*—Length — Approximately 2 mm. Seed traces have a range of size from approximately 1 to about 3 mm in length and less than 1 mm in width. Such seed traces are considered inconsequential and are normal and acceptable for seedless raisins and table grapes as a general matter.

*Commercial use.*—Generally — The present variety of grapevine is well suited for raisin production and subsequent marketing due to its seedlessness, berry size and early ripening in relative comparison to other closely similar varieties, and also in view of its high yielding characteristics. The earlier ripening date should adapt well to dry-on vine (DOV) raisin production practices which are currently being implemented in Fresno County, Calif.

*Date of harvest.*—Generally — Harvesting or cane cutting for DOV can be initiated approximately 2 to about 4 weeks ahead of Thompson Seedless grapevines growing in the same geographical vicinity due to the earlier ripening characteristics of the present new variety of grapevine. Yields are viewed as quite high. In this regard, 113 clusters were produced on the original single vine which produced 5 fruiting canes having 10 to about 15 nodes in length. This was observed during the 2000 growing season. The calculated fresh yield was 101.7 lbs. assuming an average cluster weight of 0.9 lbs.

*Soluble solids.*—As calculated on Aug. 1, 2000 the soluble solids were 23.2° Brix to produce a calculated raisin yield of 29 lbs. This assumes a 3.5:1 dry ratio.

*Resistance to pests and diseases.*—The present variety of grapevine has not demonstrated any unusual susceptibilities or resistance to common diseases or pests.

*Use.*—Variety is well suited for raisin production as noted above.

*Bud break and bud fruitfulness data.*—The original vine and two progeny vines were evaluated in the 2000 growing season. The following chart indicates the fruitfulness characteristics by node position on the canes and spurs plus latent buds on this variety.

Data collected Apr. 14, 2000. Average of 3 vines with a total of 15 canes and 5 spurs.

Cane Data by Node Position

| Node Position | 1 | 2 | 3 | 4 | 5 | 6 | 7 |
|---|---|---|---|---|---|---|---|
| % bud break | 24 | 77 | 77 | 85 | 93 | 93 | 100 |
| No. shoots/node | 0.2 | 1.0 | 0.9 | 0.9 | 1.3 | 1.1 | 1.3 |
| No. double shoots/node | 0.1 | 0.4 | 0.3 | 0.5 | 0.7 | 0.4 | 0.9 |
| % shoots bifurcated | 0 | 0 | 25 | 25 | 18 | 22 | 12 |
| % nodes fruitful | 8 | 77 | 92 | 85 | 85 | 85 | 100 |
| No. clusters/node | 0.2 | 1.2 | 1.5 | 1.6 | 2.1 | 1.6 | 1.6 |
| No. clusters/shoot | 0.7 | 1.2 | 1.6 | 1.7 | 1.6 | 1.5 | 1.2 |
| % secondary shoots fruitful | — | 100 | 100 | 100 | 100 | 100 | 100 |
| % bifurcated shoots fruitful | — | — | 100 all remaining | | | | |

| Node Position | 8 | 9 | 10 | 11 | 12 | 13 | 14 |
|---|---|---|---|---|---|---|---|
| % bud break | 100 | 93 | 100 | 100 | 90 | 100 | 100 |
| No. shoots/node | 1.4 | 1.5 | 1.7 | 1.6 | 1.4 | 1.6 | 1.7 |
| No. double shoots/node | 0.8 | 0.9 | 0.8 | 0.7 | 0.3 | 0.8 | 0.7 |
| % shoots bifurcated | 6 | 5 | 0 | 6 | 0 | 0 | 0 |
| % nodes fruitful | 92 | 85 | 100 | 100 | 90 | 89 | 100 |
| No. clusters/node | 2.5 | 2.4 | 2.6 | 2.3 | 1.5 | 2.1 | 2.3 |
| No. clusters/shoot | 1.8 | 1.6 | 1.5 | 1.4 | 1.1 | 1.4 | 1.4 |
| % secondary shoots fruitful | 100 | 88 | 100 | 86 | 75 | 100 | 100 |
| % bifurcated shoots fruitful | 100 all remaining | | | | | | |

Spur Data by Node Position

| Node Position | 1 | 2 | 3 |
|---|---|---|---|
| % bud break | 60 | 60 | 60 |
| No. shoots/node | 0.6 | 0.6 | 0.67 |
| No. double shoots/node | 0 | 0 | 0 |
| % shoots bifurcated | 0 | 0 | 20 |
| % nodes fruitful | 40 | 60 | 50 |
| No. clusters/node | 1.2 | 1.0 | 1.0 |
| No. clusters/shoot | 0.8 | 0.6 | 0.7 |
| % bifurcated shoots fruitful | — | — | 100 |

Latent Bud Data

| | |
|---|---|
| Shoots/vine | 11 |
| Cluster/vine | 3 |
| % fruitfulness | 27 |

DNA Allele sizes for 10 microsatellite DNA markers for the present variety.

| | |
|---|---|
| VVS2 | VrZAG79 |
| 135 151 | 251 257 |
| VVMD5 | VVMD6 |
| 232 238 | 194 214 |
| VVMD7 | VVMD28 |
| 239 — | 255 261 |
| VVMD27 | VVMD31 |
| 185 194 | 212 214 |
| VrZAG62 | VVMD32 |
| 193 — | 251 257 |

The above identified Allele sizes has been secured by using a simple sequence repeat or (SSR) analysis which is used worldwide on plants, animals and humans. The above identified markers (VVS2; VVMD5; etc.) have been adopted variously by the International Grape Genetics Research community such as the European Union Grape Genetic Resources Working Group as common markers to facilitate the exchange of data among grape research laboratories. It should be understood that the base pair numbers used to designate grape microsatellite alleles may differ slightly between laboratories because of differences in methodology. Still further non-numerical allele designations have not been adopted generally by the grape genetics research community. Adjustments for inter-laboratory differences can be made by referencing common cultivars that have the same alleles as the samples being analyzed.

Although the new variety of grapevine possesses the described characteristics as a result of the growing conditions prevailing in Fresno, Calif. and the central part of the San Joaquin Valley, it is to be understood that variations of the usual magnitude and characteristics incident to changes in growing conditions, fertilization, pruning and pest control are to be expected.

Having thus described and illustrated my new variety of grapevine, I claim:

1. A new and distinct variety of grapevine to be denominated varietally as F.P.C.D.O.V.#1 substantially as illustrated and described and which is characterized principally as to novelty by its production of seedless berries which are ripe for harvesting or drying-on-the-vine raisin production approximately 2 to 4 weeks ahead of the Thompson Seedless grapevines which ripen at the same geographical location.

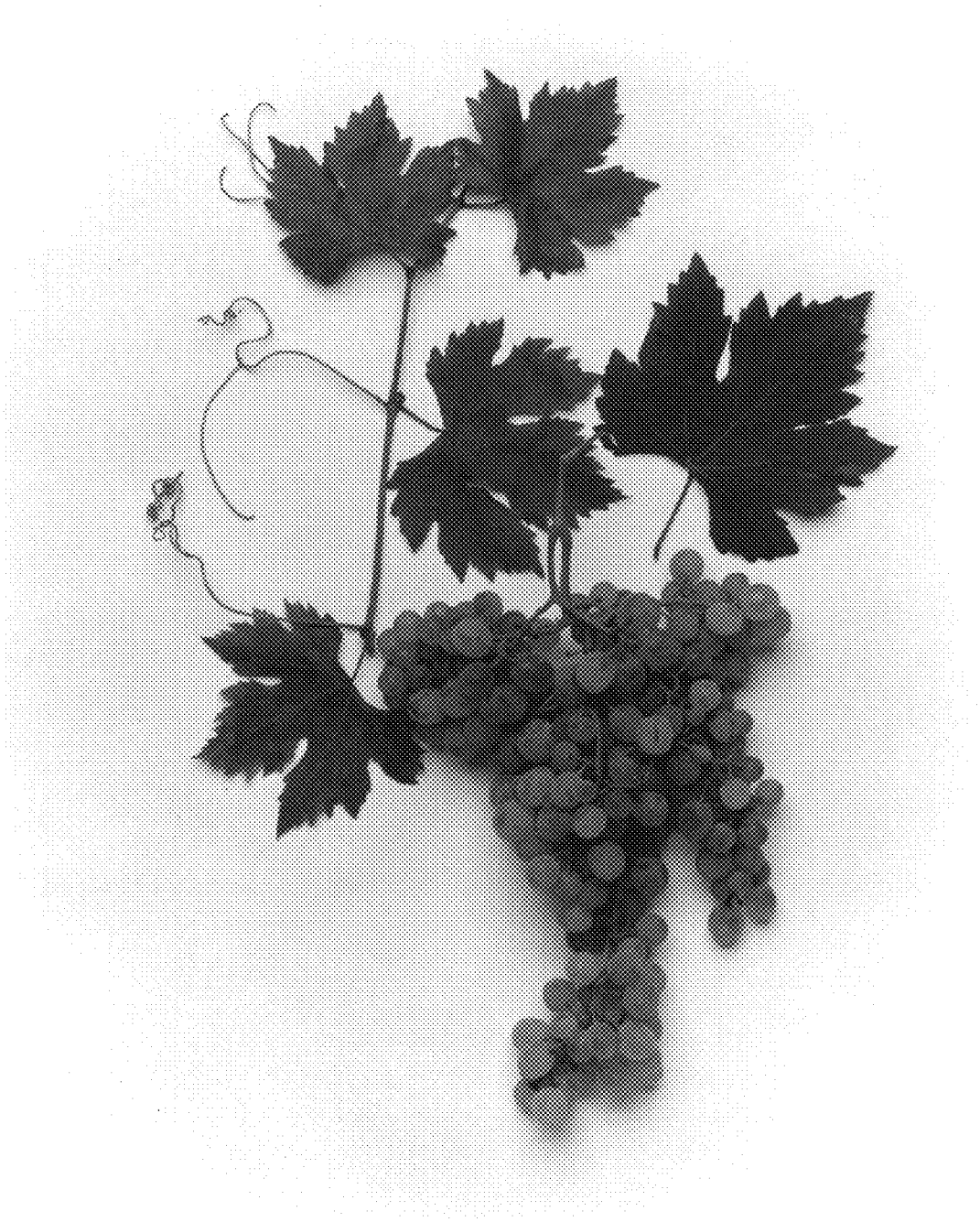

* * * * *